US009700742B2

(12) United States Patent
Canney et al.

(10) Patent No.: US 9,700,742 B2
(45) Date of Patent: *Jul. 11, 2017

(54) METHODS AND SYSTEMS FOR NON-INVASIVE TREATMENT OF TISSUE USING HIGH INTENSITY FOCUSED ULTRASOUND THERAPY

(71) Applicant: University of Washington through its Center for Communication, Seattle, WA (US)

(72) Inventors: Michael S. Canney, Menomonee Falls, WI (US); Michael R. Bailey, Seattle, WA (US); Lawrence A. Crum, Bellevue, WA (US); Vera A. Khokhlova, Seattle, WA (US); Tatiana D. Khokhlova, Seattle, WA (US); Wayne Kreider, Seattle, WA (US); Joo Ha Hwang, Bellevue, WA (US); Oleg A. Sapozhnikov, Seattle, WA (US)

(73) Assignee: University of Washington, Seattle, WA (US)

(*) Notice: Subject to any disclaimer, the term of this patent is extended or adjusted under 35 U.S.C. 154(b) by 47 days.

This patent is subject to a terminal disclaimer.

(21) Appl. No.: 14/516,442

(22) Filed: Oct. 16, 2014

(65) Prior Publication Data
US 2015/0119763 A1   Apr. 30, 2015

Related U.S. Application Data

(62) Division of application No. 13/085,368, filed on Apr. 12, 2011, now Pat. No. 8,876,740.
(Continued)

(51) Int. Cl.
*A61B 18/00* (2006.01)
*A61N 7/02* (2006.01)
(Continued)

(52) U.S. Cl.
CPC ...... *A61N 7/02* (2013.01); *A61B 2017/00084* (2013.01); *A61B 2018/00005* (2013.01); *A61B 2090/374* (2016.02); *A61B 2090/378* (2016.02)

(58) Field of Classification Search
CPC .... A61N 7/00; A61N 7/02; A61N 2007/0039; A61B 18/04
(Continued)

(56) References Cited

U.S. PATENT DOCUMENTS 6,113,558 A   9/2000   Rosenschein et al.
6,309,355 B1   10/2001   Cain et al.
(Continued)

OTHER PUBLICATIONS

Kreider, W. et al., "The Dynamics of Histotripsy Bubbles," 10th International Symposium on Therapeutic Ultrasound 2010, Jun. 9-12, 2010, Tokyo, Japan, 4 pages.
(Continued)

*Primary Examiner* — Thomas Giuliani
(74) *Attorney, Agent, or Firm* — Perkins Coie LLP

(57) ABSTRACT

Methods and systems for non-invasive treatment of tissue using high intensity focused ultrasound ("HIFU") therapy. A method of non-invasively treating tissue in accordance with an embodiment of the present technology, for example, can include positioning a focal plane of an ultrasound source at a target site in tissue. The ultrasound source can be configured to emit HIFU waves. The method can further include pulsing ultrasound energy from the ultrasound source toward the target site, and generating shock waves in the tissue to induce boiling of the tissue at the target site within milliseconds. The boiling of the tissue at least substantially emulsifies the tissue.

19 Claims, 7 Drawing Sheets

Related U.S. Application Data

(60) Provisional application No. 61/323,230, filed on Apr. 12, 2010.

(51) Int. Cl.
*A61B 17/00* (2006.01)
*A61B 90/00* (2016.01)

(58) Field of Classification Search
USPC ............... 604/22; 606/27–32; 601/3; 607/96
See application file for complete search history.

(56) References Cited

U.S. PATENT DOCUMENTS

| | | | |
|---|---|---|---|
| 7,815,641 | B2 | 10/2010 | Dodde et al. |
| 8,876,740 | B2 * | 11/2014 | Canney ............... A61N 7/02 601/3 |
| 2005/0154431 | A1 | 7/2005 | Quistgaard et al. |
| 2005/0277853 | A1 | 12/2005 | Mast et al. |
| 2007/0083120 | A1 | 4/2007 | Cain et al. |
| 2007/0179489 | A1 | 8/2007 | Dodde et al. |
| 2008/0015435 | A1 | 1/2008 | Cribbs et al. |
| 2008/0319356 | A1 | 12/2008 | Cain et al. |
| 2008/0319375 | A1 * | 12/2008 | Hardy ............... A61K 9/0009 604/22 |
| 2009/0036773 | A1 | 2/2009 | Lau et al. |
| 2009/0171254 | A1 | 7/2009 | Kushculey et al. |
| 2009/0275879 | A1 | 11/2009 | Deem et al. |
| 2010/0094178 | A1 | 4/2010 | Lacoste |
| 2011/0054315 | A1 | 3/2011 | Roberts et al. |
| 2011/0054363 | A1 | 3/2011 | Cain et al. |
| 2011/0251528 | A1 | 10/2011 | Canney et al. |

OTHER PUBLICATIONS

Canny, M. et al., "Shock-Induced Heating and Millisecond Boiling in Gels and Tissue Due to High Intensity Focused Ultrasound," Ultrasound in Medicine & Biology, Sep. 18, 2009, pp. 250-267.

Canny, M. et al., "Tissue Erosion Using Shock Wave Heating and Millisecond Boiling in HIFU Field," 9th International Symposium on Therapeutic Ultrasound, AIP Conference Proceedings, vol. 1215, 2010, pp. 36-39.

Bessonova, O. et al., "Nonlinear Derating Method for High Intensity Focused Ultrasound (HIFU) Fields," 2009 IEEE International Ultrasonics Symposium Proceedings, pp. 216-219.

Bessonova, O. et al., "A Derating Method for Therapeutic Applications of High Intensity Focused Ultrasound," Journal of Acoust Phys., Jan. 1, 2010, pp. 354-363.

Canney, M. et al., "Acoustic Characterization of High Intensity Focused Ultrasound Field: A Combiled Measurement and Modeling Approach," Journal of Acoust Soc Am., Oct. 2008, pp. 2406-2420.

Khokhlova, T. et al., "Millisecond Bursts of Focused Ultrasound Shock Waves to Produce Boiling and Tissue Emulsification," Submittied as a regular research paper for the Special Issue on the Acoustics of Bubbles and Cavitation (ABC), 2011, 41 pages.

* cited by examiner

METHODS AND SYSTEMS FOR NON-INVASIVE TREATMENT OF TISSUE USING HIGH INTENSITY FOCUSED ULTRASOUND THERAPY

CROSS-REFERENCE TO RELATED APPLICATION(S)

This application is a divisional of U.S. application Ser. No. 13/085,368, filed Apr. 12, 2011, now U.S. Pat. No. 8,876,740 which claims the benefit of U.S. Provisional Application No. 61/323,230, entitled "METHODS AND SYSTEMS FOR NON-INVASIVE TREATMENT OF TISSUE USING HIGH INTENSITY FOCUSED ULTRASOUND THERAPY," filed Apr. 12, 2010, and incorporated herein by reference in its entirety.

STATEMENT REGARDING FEDERALLY SPONSORED RESEARCH OR DEVELOPMENT

This disclosure was made with government support under grant number EB007643 awarded by National Institutes of Health (NIH)-Federal Reporting and grant number SMST01601 awarded by National Space Biomedical Research Institute (NSBRI). The government has certain rights in the invention.

TECHNICAL FIELD

The present technology relates generally to high intensity focused ultrasound. In particular, several embodiments are directed toward methods and systems for non-invasive treatment of tissue using high intensity focused ultrasound therapy.

BACKGROUND

Minimally invasive and non-invasive therapeutic ultrasound treatments can be used to ablate, necrotize, and/or otherwise damage tissue. High intensity focused ultrasound ("HIFU"), for example, is used to thermally or mechanically damage tissue. HIFU thermal treatments increase the temperature of tissue at a focal region such that the tissue quickly forms a thermally coagulated treatment volume. HIFU treatments can also cause mechanical disruption of tissue with well-demarcated regions of mechanically emulsified treatment volumes that have little remaining cellular integrity. For certain medical applications, tissue emulsification may be more favorable than thermal damage because it produces liquefied volumes that can be more easily removed or absorbed by the body than thermally coagulated solid volumes.

HIFU treatments can utilize a sequence of pulses, rather than continuous-wave HIFU exposures, to reduce undesirable thermal effects on the surrounding tissue. In histotripsy exposures, for example, HIFU sources operate with low duty cycles (e.g., 1%), use relatively short pulses (e.g., 10-20 microseconds), and deliver high pulse average intensities of up to 40 kW/cm$^2$ to form bubbles that mechanically disrupt tissue. Histotripsy techniques, for example, can induce cavitation by delivering pulses of high peak negative pressures that are significantly higher than the tensile strength of the tissue. The repetition of such pulses can increase the area of tissue affected by cavitation to create a "cavitation cloud" that emulsifies the tissue. Cavitation, however, is generally stochastic in nature, making cavitation-based HIFU treatments somewhat unpredictable and difficult to reproduce. For example, cavitation activity can stop unexpectedly during the course of the treatment, resulting in the extinction of the cavitation cloud and termination of the desired tissue emulsification. Very high peak negative pressures of about −20 MPa are required to initiate and maintain the cavitation cloud. To reach these peak negative pressure levels, large aperture transducers with high focusing angles and high power output capabilities are necessary. Therefore, there is a need to enhance the reliability, predictability, and consistency of mechanical disruption of tissue damage (e.g., emulsification), while operating at lower pressure levels and still limiting thermal coagulation of the target tissue and the surrounding tissue.

DETAILED DESCRIPTION

The present technology is directed toward methods and systems for non-invasively treating tissue using HIFU. In several embodiments, for example, a HIFU pulsing protocol can generate shock waves at a target site that induce millisecond boiling to mechanically damage tissue with little to no thermal effect. The pulsing protocol can take into account peak positive pressure, shock wave amplitude, ultrasound frequency, pulse repetition frequency, pulse length, duty cycle, and/or other factors that induce mechanical fractionation of tissue. Additionally, HIFU systems and methods in accordance with the present technology can detect boiling and/or tissue erosion to identify and differentiate mechanical effects from thermal effects of HIFU treatment. These HIFU systems and methods have a number of both therapeutic and cosmetic applications, such as producing bulk ablation of benign and malignant tumors.

Certain specific details are set forth in the following description and in FIGS. 1A-4C to provide a thorough understanding of various embodiments of the technology. For example, several embodiments of HIFU treatments that destroy tissue are described in detail below. The present technology, however, may be used to destroy multi-cell structures similar to tissue. Additionally, the term "target site" is used broadly throughout the disclosure to refer to any volume or region of tissue that may benefit from HIFU treatment. Other details describing well-known structures and systems often associated with ultrasound systems and associated devices have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1A-4C.

Figure 1A:
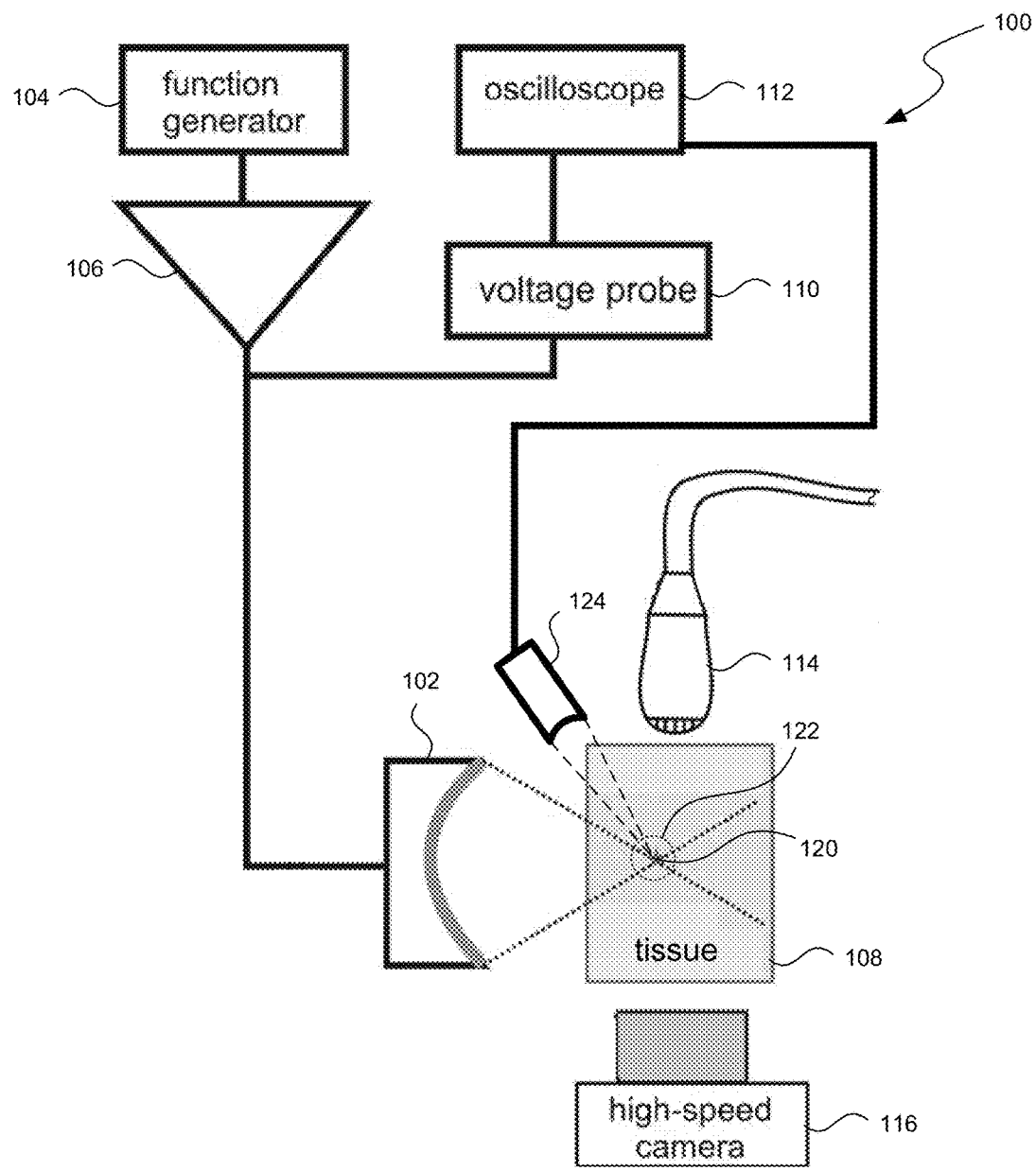
FIG. 1A is a schematic view of a HIFU system configured in accordance with an embodiment of the present technology.

FIG. 1A is a schematic view of a HIFU system 100 configured in accordance with an embodiment of the present technology. The HIFU system 100 can include a HIFU source 102 operably coupled to a function generator 104 and an amplifier. The HIFU source 102 can be an ultrasound transducer that emits high levels of ultrasound energy to a focus 120. The focus 120 can be a point, plane, or region at which the intensity from the HIFU source 102 is the highest. In other embodiments, the HIFU source 102 can include a single-element device, a multi-element device, an extracorporeal device, an intracavitary device, and/or other devices or systems configured to emit HIFU energy to a focus. The HIFU source 102 can have a frequency range of approximately 0.5-20 MHz. In other embodiments, the frequency of the HIFU source 102 can vary. The function generator 104 (e.g., an Agilent 33250A function generator from Agilent of Palo Alto, Calif.) and the amplifier 106 (e.g., an ENI A-300 300 W RF amplifier from ENI of Rochester, N.Y.) can drive the HIFU source 102 to generate pulsed shock waves proximate to the focus 120. Accordingly, the HIFU system 100 can implement a pulsing protocol in which ultrasound frequency, pulse repetition frequency, pulse length, duty cycle, pressure amplitude, and/or other factors associated with the HIFU treatment can be adjusted to generate shock waves proximate to the focus 120.

Figure 1B:
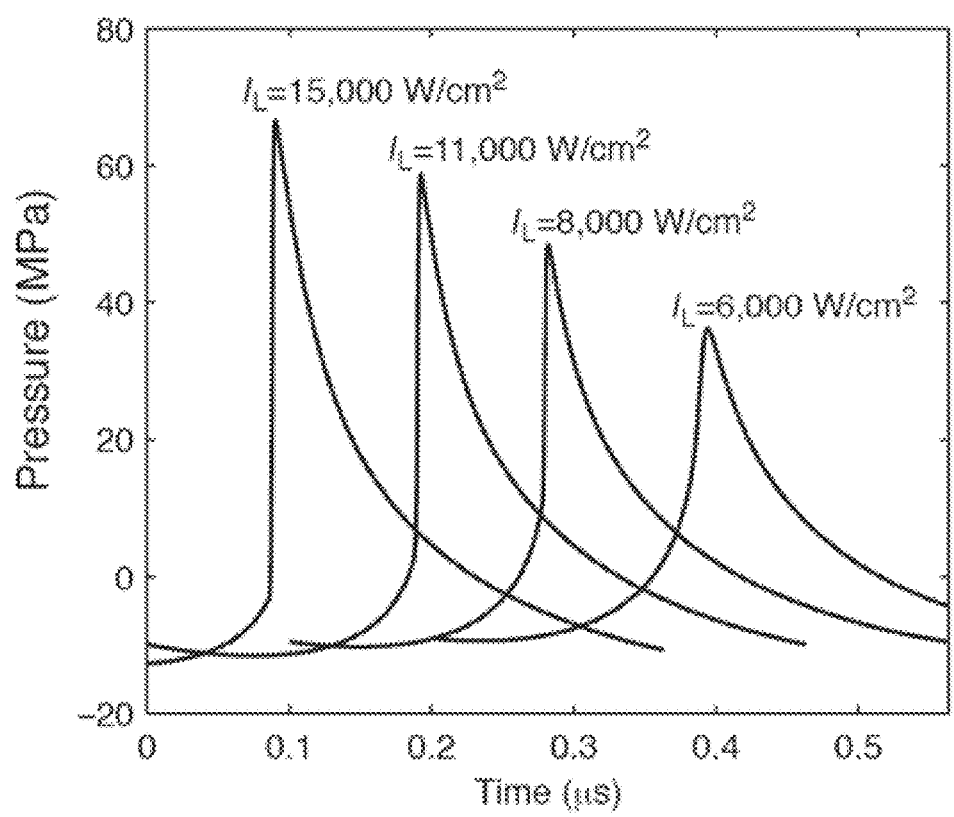
FIG. 1B is a graph illustrating focal pressure waveforms modeled in tissue in accordance with several embodiments of the present technology.

Without being bound by theory, it was generally thought that shock waves could not form in tissue due to the losses in amplitude caused by the degradation of focusing in inhomogeneous tissue and the rapid absorption of higher harmonic frequencies in the tissue along the propagation path between a target and an ultrasound source. However, the present inventors have shown that shock waves can, in fact, form within tissue when used with suitable HIFU systems (e.g., the HIFU system 100). FIG. 1B, for example, is a graph illustrating modeled focal waveform levels in tissue produced by the HIFU system 100. The HIFU system 100 can deliver pulsed high intensities (e.g., between approximately 6 kW/cm$^2$ and 15 kW/cm$^2$) at the focus 120 to generate shock waves having amplitudes greater than approximately 30 MPa. In other embodiments, the shock wave amplitudes and intensities of the HIFU system 100 can be greater or smaller. Advantageously, the shock waves can enhance heating of the tissue to induce rapid boiling.

Referring back to FIG. 1A, during treatment the HIFU source 102 can be positioned proximate to a tissue 108, and the focus 120 of the HIFU source 102 can be aligned with at least a portion of a target site 122 within the tissue 108. For example, the HIFU source 102 can be positioned over a patient's kidney, heart, or liver, and the focus 120 can be aligned with infected or otherwise adverse tissue therein. Larger target sites 122 can be mechanically fractionated by scanning the HIFU source 102 over the treatment region using either mechanical or electronic scanning Such scanning and the initial positioning of the HIFU source 102 can be performed manually or mechanically (e.g., using a three-axis positioning system, not shown). The function generator 104 can initiate the pulsing protocol to generate shock waves with amplitudes between approximately 30 MPa and approximately 80 MPa at the focus 120 with the HIFU source 102 having a frequency of approximately 2 MHz. In other embodiments, such as at lower or higher ultrasound frequencies, the shock wave amplitudes of the HIFU source 102 can be greater or smaller. Absorption of ultrasonic energy occurs primarily at the shock front (e.g., shown in FIG. 1B), and induces rapid heating of the tissue 108 that can boil the tissue 108 within milliseconds. For example, the amplitude of the shock wave can be such that it causes tissue boiling in less than 10 ms. Depending upon the power driving the HIFU system 100 and/or the acoustic parameters of the tissue 108, the time-to-boil can be greater or less than 10 ms.

The HIFU system 100 can be configured such that the duration of each pulse is at least equivalent to the time necessary to induce tissue boiling at approximately 100° C. Therefore, during each pulse, one or more boiling bubbles can be formed in the tissue 108. In several embodiments, the boiling bubbles can have cross-sectional dimensions of approximately 2-4 mm when the ultrasound frequency is approximately 2 MHz. In other embodiments, however, the boiling bubbles can be larger or smaller. For example, the boiling bubbles in the tissue 108 can have a cross-sectional dimension between approximately 100 μm and approximately 4 mm on the order of the beam-width of the ultrasound source 102 at the focus 120. The superheated vapor of the boiling bubbles provides a force pushing outward from the bubble. This repetitive explosive boiling activity and interaction of the ultrasound shock waves with the boiling bubbles emulsifies the tissue 108 at the target site 122 to form a liquid-filled lesion devoid of cellular structure, with little to no thermal coagulation within the treated region. The reflection of the shock wave from the surface of these millimeter-sized boiling bubbles can also form cavitation bubbles proximate to the boiling bubble that can also induce mechanical damage to tissue.

Mechanical tissue destruction can occur consistently within localized treatment volumes when the temperature of the tissue reaches 100° C. and boiling bubbles form during each pulse or after a series of consecutive pulses. For example, boiling bubbles are generally produced proximate to the focus 120 of the HIFU source 102 (i.e., where shock wave amplitude is the highest), unlike cavitation that occurs randomly over a larger region. In selected embodiments, the energy deposition of the ultrasound beam can focus within 100 microns of the target site 122. Additionally, unlike peak negative pressures that induce cavitation and continuously grow the treatment volume, the peak positive pressures that induce boiling bubbles can maintain relatively defined treatment volumes. Moreover, the present method of using shock waves to rapidly heat tissue to boiling allows the HIFU system 100 to penetrate target sites deeper within the tissue 108 than cavitation-based HIFU techniques that require higher pressures to deliver to the focus through absorptive tissue. Boiling bubbles can also be much larger (e.g., approximately 2-4 mm) than individual cavitation bubbles that must randomly coalesce to produce any beneficial treatment volume. Therefore, the shock wave heating and millisecond boiling generated by the HIFU system 100 provides a highly repeatable, localizable, and predictable mechanical destruction of the tissue 108 at lower pressure levels as compared to cavitation.

In selected embodiments, the pulsing protocol of the HIFU system 100 can be adjusted to minimize the deposition of the HIFU energy in the tissue 108, and thereby reduce the thermal effects (e.g., thermal coagulation, necrotized tissue) of the HIFU treatment. For example, repeating shock waves at a pulse repetition frequency that is slow enough (e.g., approximately 1 Hz or 1% duty cycle) to allow cooling between the pulses such that lesion content within the target site 122 and the surrounding tissue 108 shows minimal to no evidence of thermal denature. A duty cycle of less than approximately 10% also allows cooling between pulses that minimizes thermal denature. In selected embodiments, the duration of the pulses can be reduced over the course of the pulsing protocol to account for a decreasing time to boil caused by the retention of heat in the tissue 108 between pulses. Additionally, the duration of each pulse can be such that the thermally denatured volume of the tissue 108 within each pulse is negligible. For example, in selected embodiments, the duration of each pulse is less than approximately 10 ms. In other embodiments, the pulse length can be longer.

Figure 1C:
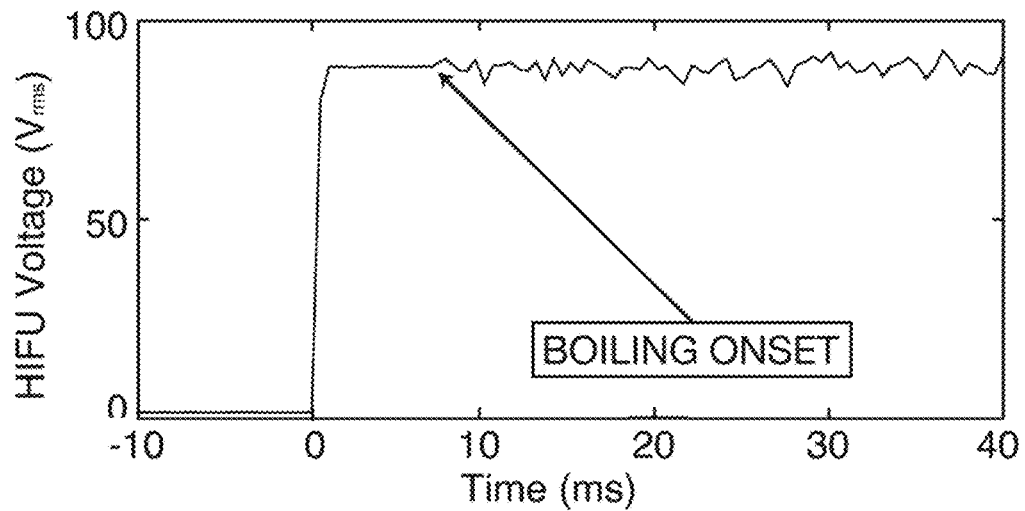
FIG. 1C is a graph illustrating fluctuations in HIFU source drive voltage in accordance with an embodiment of the present technology.

The HIFU system 100 can also include systems or devices that detect and monitor boiling initiation and the bubble activity in the tissue 108. These devices can be used during treatment to distinguish boiling bubbles from cavitation bubbles and ensure the pulsing protocol induces the desired boiling bubbles at the target site 122. In the embodiment illustrated in FIG. 1A, for example, the HIFU source 102 is operably coupled to a voltage probe 110 and an oscilloscope 112 that can monitor and record, respectively, the drive voltage at the HIFU source 102. FIG. 1C is a graph illustrating a recorded drive voltage during HIFU treatment in accordance with an embodiment of the present technology. Fluctuations in the drive voltage indicate the onset of boiling bubbles and can be distinguished from lower levels of fluctuations that are caused by cavitation activity. In the embodiment illustrated in FIG. 1C, the drive voltage begins to fluctuate within 10 ms of the HIFU pulse, and thus indicates the presence of boiling bubbles within 10 ms of the HIFU pulse. In other embodiments, the time-to-boil can be shorter or longer.

Figure 1D:
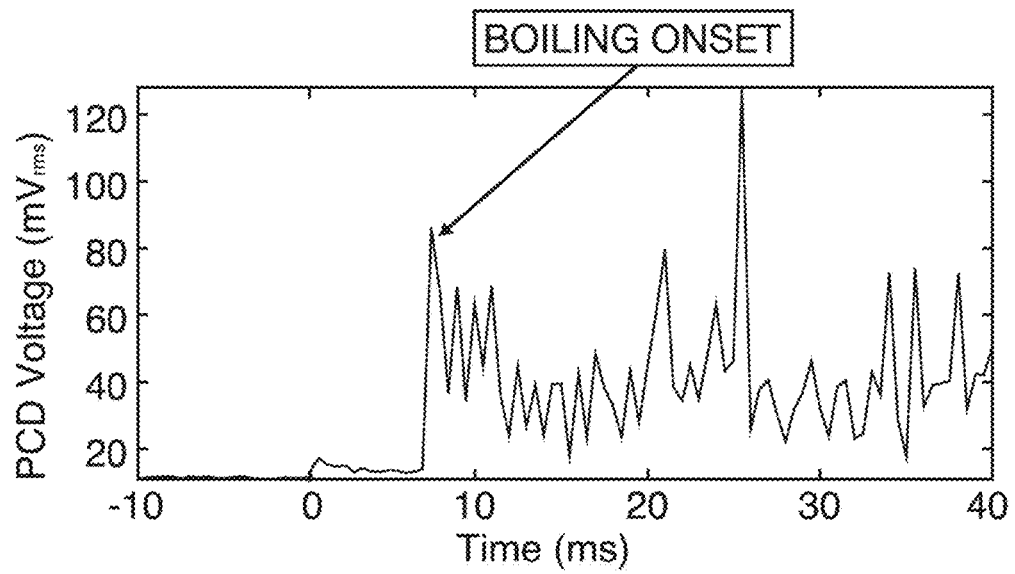
FIG. 1D is a graph illustrating acoustic signals received by a passive cavitation detection system during a HIFU treatment in accordance with an embodiment of the present technology.

Referring back to FIG. 1A, the HIFU system 100 can also include a passive cavitation detector ("PCD") 124 that monitors acoustic signals associated with boiling. For example, the PCD 124 can include an acoustic receiver (e.g., an ultrasound transducer) separate from the HIFU source 102, but confocally aligned with the focus 120 of the HIFU source 102 such that the PCD 124 can receive real-time acoustic feedback during HIFU treatment. In general, boiling bubbles scatter frequencies that already exist in the incident wave, whereas cavitation bubbles create short pops when they collapse and have a broadband frequency noise. Boiling bubbles may also generate lower frequency noise (e.g., kilohertz frequencies) that can be recorded and used to monitor treatments. As shown in FIG. 1A, similar to the voltage probe 110, the PCD 124 can also be coupled to the oscilloscope 112 to record acoustic signals during HIFU treatment. FIG. 1D, for example, is a graph illustrating acoustic signals during HIFU treatment in accordance with an embodiment of the present technology. The graph shows that a large change in the PCD signal amplitudes caused by boiling bubbles, begin within 10 ms of the first HIFU pulse. In other embodiments, however, the boiling bubbles can occur sooner or later during the HIFU pulse.

Echogenic boiling activity and/or the thermal effects of the HIFU treatment can also be monitored using separate devices and systems. The HIFU system 100 illustrated in FIG. 1A, for example, includes an imaging system 114 that can create a visual image to monitor the boiling bubbles and thus temperatures of approximately 100° C. in real-time at a depth within the tissue 108. The imaging system 114 can be a separate confocal transducer, an unfocused transducer, another type of confocal or unfocused ultrasound source, one or more sub-element(s) of a multi-element array, and/or a separate imaging system. For example, in one embodiment the imaging system 114 includes an HDI-1000 scanner with a CL 10-5 scanhead made by Philips Medical Systems of Bothell, Wash. In other embodiments, the imaging system 114 can include a magnetic resonance imaging ("MRI") system that can monitor temperature and boiling activity during HIFU treatments.

Additionally, as shown in FIG. 1A, the HIFU system 100 can include a high-speed camera 116 (e.g., video, still frame) that can take video or still images of the target site 122 during HIFU treatment to capture the effects of the HIFU treatment on the tissue 108. Such a camera 116 must generally be used with initially transparent tissues or tissue phantoms to capture the thermal effects of HIFU treatment within the tissue 108. Accordingly, the high-speed camera 116 can be especially suited for experiments and testing that include transparent gel phantoms to simulate tissue.

The HIFU system 100 can also simulate the shock waves and heating in water or tissue. Resultant modeling can be used to calculate heating from the shock amplitude of the focal waveform, and for extrapolating pressure waveforms at the focus 120 in water to the equivalent waveforms in tissue. One such method for this extrapolation is called "derating," and is useful for regulatory oversight and HIFU treatment planning. For example, derating can be used to determine values of the acoustic field parameters in the tissue region exposed to HIFU (e.g., the target site 122 and the surrounding tissue 108). During the derating process, low level ultrasound measurements can be taken at the focus 120 in water and scaled to the higher level outputs used during therapeutic HIFU treatments. To obtain in situ acoustic parameters, the corresponding values in water are scaled to account for losses that occur over the propagation path in tissue. This derating procedure assumes linear wave propagation both in water and in tissue. However, the high acoustic intensities associated with the present HIFU system 100 cause nonlinear propagation effects that cause the formation of shock waves in the focus 120 (i.e., where the pressure is the highest) of the HIFU source 102. As such, the nonlinear propagation can be taken into account by comparing the pressures at the HIFU source 102 that produce the same focal waveforms calculated or measured in water and in tissue. The linear attenuation in the tissue at the source frequency can provide a scaling factor that accounts for losses over the wave propagation in tissue. This scaling factor can be used to determine optimal parameters (e.g., peak positive pressure) of the pulsing protocol to achieve controlled tissue emulsification. U.S. Provisional Application No. 61/384,108, entitled "A DERATING METHOD FOR THERAPEUTIC APPLICATIONS OF HIGH INTENSITY FOCUSED ULTRASOUND," filed Sep. 17, 2010, further discloses such a derating method, and is incorporated herein by reference in its entirety.

The derating process in conjunction with the HIFU system 100 can implement a refined pulsing protocol that mechanically damages tissue, while minimizing thermal denature. For example, the requisite power for effective HIFU treatment can be calculated for different parts of the body by taking into account the type of tissue (e.g., the losses of ultrasound energy in the tissue prefocally) and the size of the ultrasound source 102. As such, the HIFU system 100 can be used to emulsify malignant or benign tumors in the prostate, kidneys, and/or other body parts. The HIFU system 100 can also be used to cut through tissue. For example, the localized HIFU treatment can cut through the heart septum to non-invasively treat heart defects. In other embodiments, the HIFU system 100 can be used to treat other tissues within the body.

Figure 2:
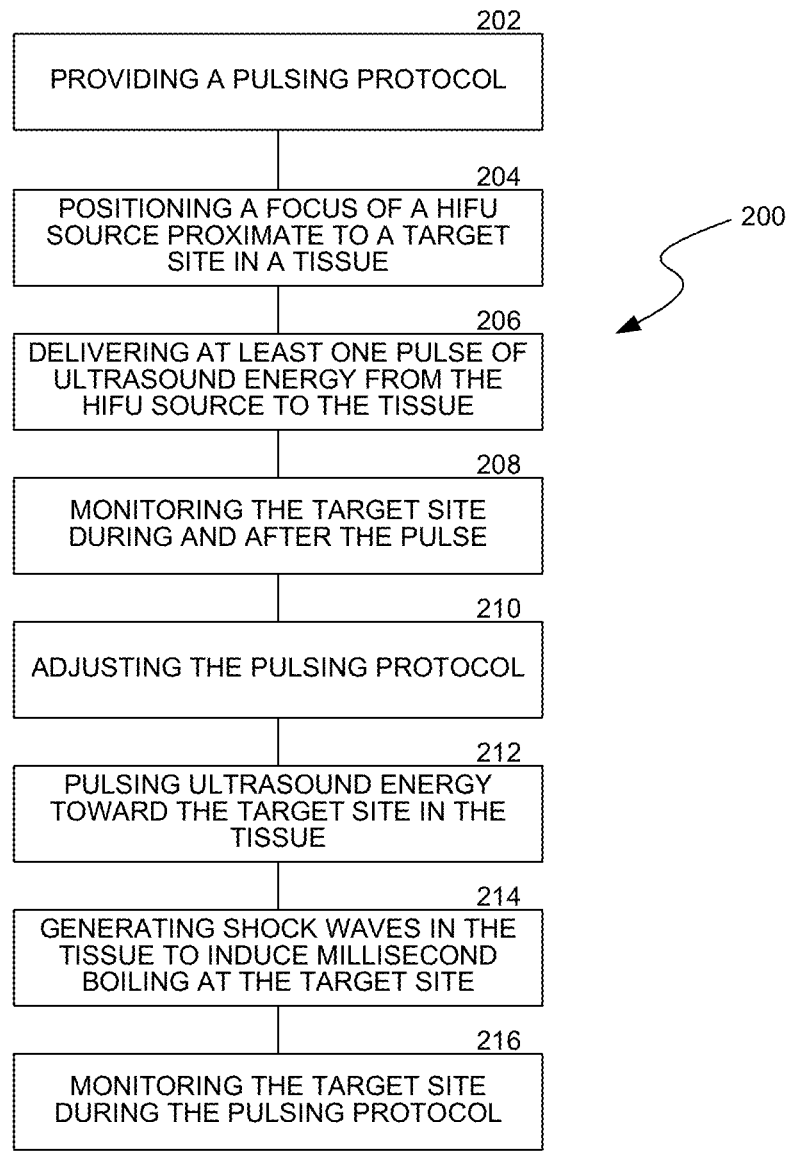
FIG. 2 is a block diagram illustrating a method of treating tissue at a target site in accordance with an embodiment of the present technology.

FIG. 2 is a block diagram illustrating a method 200 of treating a target tissue site in accordance with an embodiment of the present technology. The method 200 can include providing a pulsing protocol (block 202). As discussed above, pulsing protocols can include a variety of different factors that can induce millisecond boiling with little to no thermal denature in and around the lesion. For example, a pulsing protocol can take into account the ultrasound frequency at a HIFU source, peak positive pressure at the focus, shock amplitude, pulse length, pulse repetition frequency, and duty cycle. In other embodiments, additional factors related to tissue boiling and shock wave heating can be included in the pulsing protocol. In selected embodiments, a derating process can be used to estimate values of acoustic field parameters of the exposed tissue, and therefrom calculate the requisite peak positive pressures and pulse lengths for shock wave heating and millisecond boiling. The pulsing protocol can also be configured to minimize thermal effects of the HIFU treatment on the tissue. For example, as described above, the duty cycle can be less than 10% to ensure sufficient cooling occurs between shock wave pulses and prevent thermal denature. As another example, the pulse length can be less than approximately 100 ms such that any thermally denatured volume formed within each pulse is negligible.

Once the pulsing protocol is established, the method 200 can continue by positioning a focus of a HIFU source proximate to a target site in a tissue (block 204). The HIFU source can include generally similar features as the HIFU source 102 described above with reference to FIG. 1A. For example, the HIFU source can generate shock waves at the focus with amplitudes between approximately 30 MPa and approximately 80 MPa for ultrasound sources operating at frequencies of approximately 2 MHz. In other embodiments, the shock waves can have amplitudes between approximately 10 MPa and approximately 100 MPa for ultrasound sources that have frequencies between approximately 0.5-20 MHz. As discussed above, the focus of the HIFU source can be mechanically or manually aligned with the target site.

Optionally, the method 200 can include delivering at least one pulse of ultrasound energy from the HIFU source to the tissue (block 206), and monitoring the target site in real-time during and/or after the pulse (block 208). For example, a test pulse can be delivered to the target site, and the drive voltage and/or the acoustic signal can be interpreted to determine whether the requisite millisecond boiling occurred. Fluctuations in the drive voltage monitored by a voltage probe and/or scattered frequencies of the acoustic signal recorded by a PCD system or other acoustic receivers can indicate that the desired boiling bubbles are generated during HIFU treatment (i.e., acoustic pulsing). In other embodiments, images of the target site can be taken during the test pulse with a B-mode ultrasound transducer and/or other imaging systems to visually identify the thermal effects at the target site. When boiling is not identified during the test pulse and/or thermal destruction occurs, the method 200 can continue by adjusting the pulsing protocol such that it induces boiling during substantially every pulse (block 210). For example, the pulse length, and/or the power can be increased to ensure boiling during each pulse. As another example, the duty cycle, pulse length, and/or shock wave amplitude at the focus can be decreased to prevent thermal tissue destruction (e.g., coagulation).

The method 200 can continue by pulsing ultrasound energy toward the target site in the tissue (block 212). Each pulse of shock waves at the target site can generate boiling bubbles within milliseconds. For example, shock waves with amplitudes between approximately 30 MPa and approximately 80 MPa delivered at a HIFU source frequency of approximately 2 MHz, and a peak power between approximately 10-25 kW can induce boiling bubbles within 10 ms. This rapid millisecond boiling can mechanically disrupt the tissue without evident thermal damage. For example, the pulse lengths can be short enough (e.g., below approximately 40 ms) to substantially prevent thermally denature within or around the lesion. Additionally, as described above, the HIFU source can deliver shock waves to its focus to consistently induce boiling within a localized treatment area. Therefore, the millisecond boiling provided by this HIFU method 200 provides a repeatable, localizable, and predictable mechanical destruction of tissue. Optionally, the target site can be monitored during HIFU treatment to ensure boiling and/or otherwise observe the effects of the HIFU treatment (block 216). The method 200 can continue until the desired target site is mechanically fractionated or otherwise destroyed.

Figure 3A:
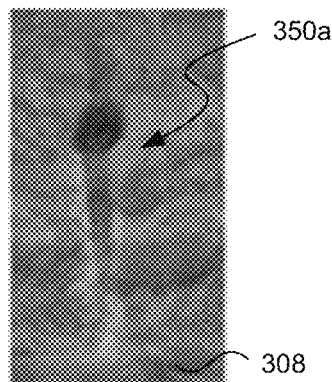
FIGS. 3A-3C are photographs of various types of lesions formed in tissue using HIFU in accordance with embodiments of the present technology.
Figure 3B:
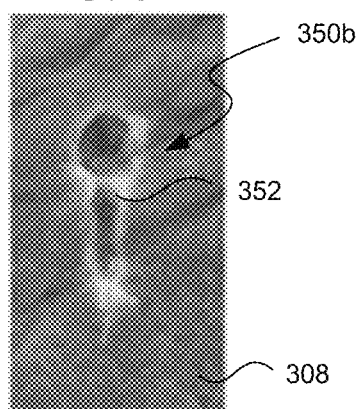
Figure 3C:
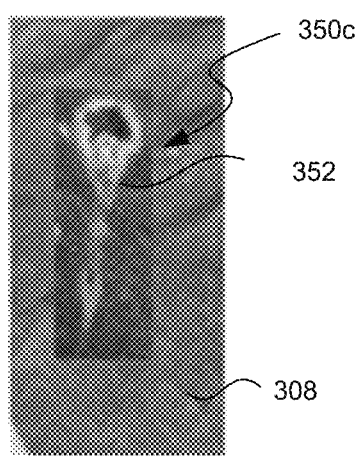

FIGS. 3A-3C are photographs of various types of lesions 350 (identified individual as a first lesion 350a, a second lesion 350b, and a third lesion 350c) formed in tissue 308 using a pulsing protocol in accordance with embodiments of the present technology. The lesions 350 were produced with an ultrasound source operating at a frequency of approximately 2 MHz and a total "HIFU on" duration of approximately 500 ms and a constant power to a HIFU source within each pulse. FIGS. 3A-3C show the progressive increase of the pulse duration (e.g., between 200 microseconds and 500 milliseconds) and/or duty cycle (between 0.3% and 100%). Purely mechanical damage occurred with duty cycles of approximately 2% or less and pulse durations of less than 30 ms (i.e., 3-10 times the time-to-boil). For example, the first lesion 350a shown in FIG. 3A illustrates purely mechanical damage that includes a cavity or void filled with liquefied tissue (for clarity, liquefied tissue is removed). The liquid is the same color as the unaffected tissue 308, and can be easily poured from the void.

Increasing the duty cycle and/or the pulse duration of the pulsing protocol can result in the second lesion 350b shown in FIG. 3B that includes a combination of mechanical and thermal damage. The second lesion 350b includes a void similar to that of the first lesion 350a, but is filled with a white paste. Like the liquefied tissue of the first lesion 350a, the white paste can be easily removed from the void. Additionally, as shown in FIG. 3B, the second lesion 350b has coagulated edges 352 (e.g., indicated by the lighter tissue). Both the white paste that fills the void and the coagulated edges 354 indicate that the thermal exposure during HIFU treatment was too long to avoid thermal tissue damage. Further increasing the pulse duration and/or duty cycle can result in the third lesion 350c shown in FIG. 3C. The third lesion 350c is a solid thermal lesion with coagulated edges 352 and an evaporated core. In this embodiment, the purely thermal damages to the tissue 308 occurred with pulses longer than 100 ms or a duty cycle exceeding approximately 10%.

As further shown in FIGS. 3A-3C, the lesions 350 can form a tadpole-like shape. The focus of the HIFU source (e.g., the HIFU source 102 shown in FIG. 1A) is generally at the "tail" end of the lesion 350 and the larger cavity or void is oriented closer to the HIFU source.

Figure 4A:
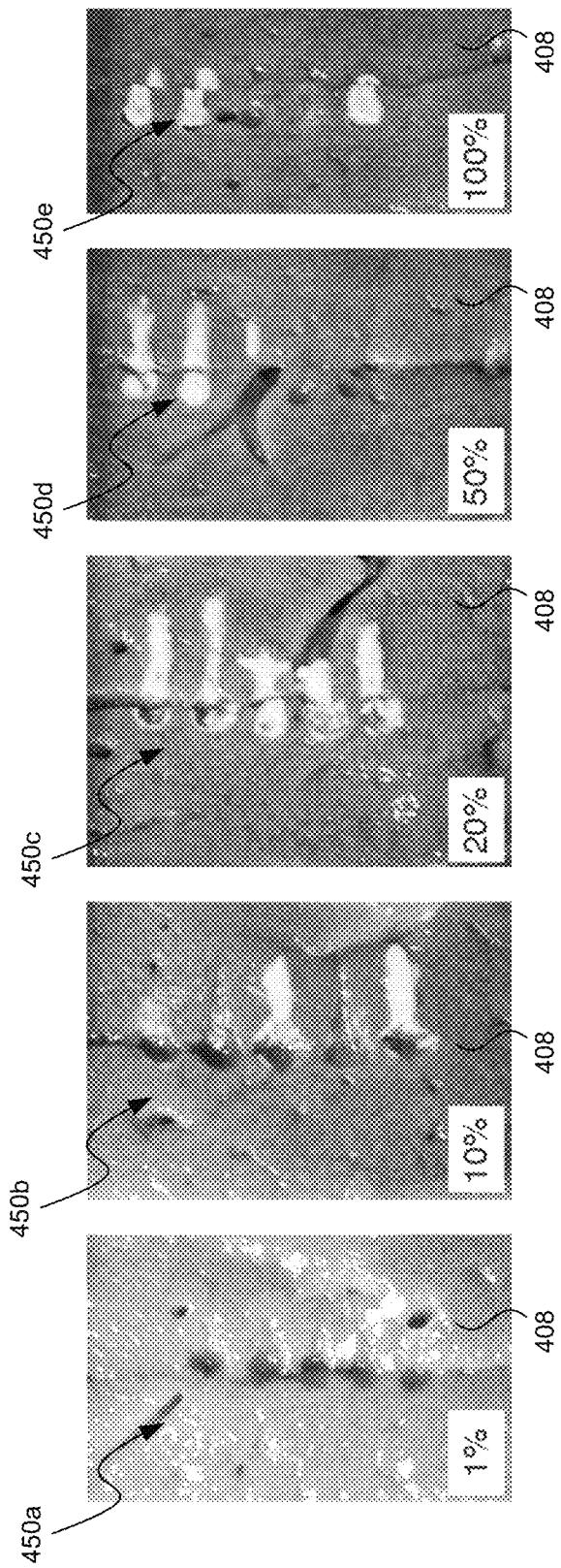
FIG. 4A-4C illustrate various lesions formed in tissue using HIFU in which duty cycle, pulse length, and power, respectively, were varied in accordance with embodiments of the present technology.
Figures 4B, 4C:
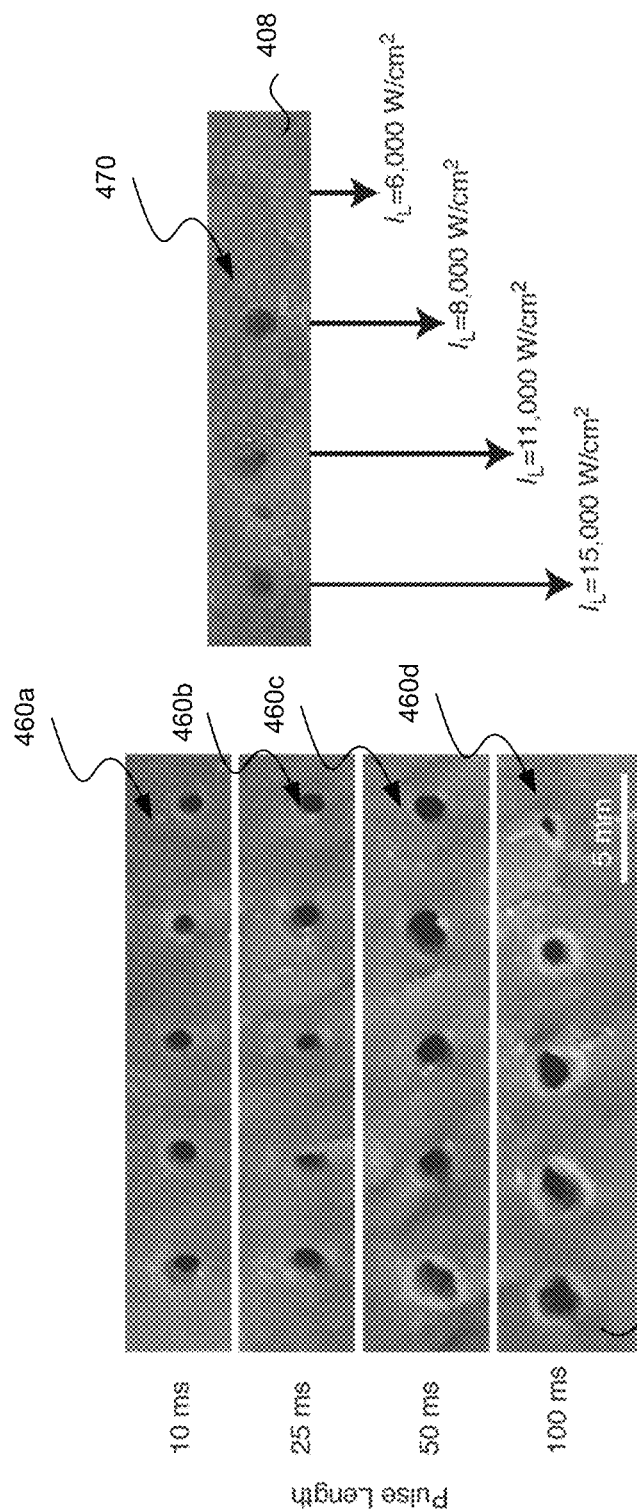

FIGS. 4A-4C illustrate lesions formed in tissue 408 (e.g., liver and heart tissue) using HIFU treatments which vary duty cycle, pulse length, and power, respectively, in accordance with embodiments of the present technology. More specifically, FIG. 4A illustrates various lesions 450 (identified individually as first through fifth lesions 450a-e, respectively) formed in liver tissue using HIFU treatments in which the duty cycle was varied between 1% and 100% (i.e., continuous exposure) with a mean time to boil of approximately 3.7 ms. As with the lesions 350 described above with reference to FIGS. 3A-3C, as the duty cycle increases, the lesions contained increasing amounts of thermal damage (e.g., coagulation, white paste) with less evident mechanical damage.

FIG. 4B illustrates various lesions 460 (identified individually as first through fourth lesions 460a-d, respectively) formed in heart tissue using HIFU treatments in which the pulse length was varied between 10 ms and 100 ms. The duty cycle was maintained at 1%, and the total HIFU treatment time was 500 ms. Boiling was generally induced at approximately 3.3 ms. As shown in FIG. 4B, even though the pulse length increased, the damage induced to the tissue 408 was mostly mechanical as evidenced by the minimal amount of blanched tissue surrounding the lesions 460.

FIG. 4C illustrates various lesions 470 formed in tissue using HIFU treatments in which the power to the HIFU source was varied such that the focal waveform was changed from a non-linearly distorted waveform to a full shock wave. As shown in FIG. 4C, the non-linearly distorted wave with an intensity of 6,000 W/cm$^2$ did not form a lesion. However, increasing the power to form shock waves did cause mechanical damage shown as the lesions 470. Additionally, in this embodiment, the peak positive pressure was changed from 36 MPa to 70 MPa, while the peak negative pressure was steadily maintained (i.e., between 9 and 12 MPa) at a pressure lower than that necessary to induce cavitation damage to tissue. Thus, FIG. 4C shows that the shock waves with amplitudes mainly defined by peak positive pressures were the source of mechanical tissue damage, rather than cavitation.

From the foregoing, it will be appreciated that specific embodiments of the technology have been described herein for purposes of illustration, but that various modifications may be made without deviating from the disclosure. For example, the HIFU system 100 of FIG. 1A can include additional devices and/or systems to facilitate shock wave heating and millisecond boiling of the tissue 108. For example, the HIFU system 100 can include a timing board to trigger the function generator 104, additional amplifiers 106, high-pass or other suitable filters, a computer to drive the entire HIFU system 100, and/or other suitable devices related to HIFU treatments. Certain aspects of the new technology described in the context of particular embodiments may be combined or eliminated in other embodiments. For example, the HIFU system 100 does not need to include some of the devices shown in FIG. 1A. In selected embodiments, the HIFU system can include only one of or a combination of the voltage probe 110, the PCD 124, the imaging system 114, and/or the high-speed camera 116 to monitor the thermal and mechanical effects of the HIFU treatment. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A high intensity focused ultrasound (HIFU) system for treating tissue, the HIFU system comprising: an ultrasound source having a frequency range between approximately 0.5 MHz and approximately 20 MHz, the ultrasound source being configured to deliver a peak positive pressure between approximately 10 MPa and approximately 100 MPa, wherein the ultrasound source is configured to generate shock waves proximate to a target site in the tissue and distinct from shock waves resulting from cavitation; a function generator operably coupled to the ultrasound source, the function generator being configured to generate a pulsing protocol delivered by the ultrasound source to the target site of tissue, wherein the pulsing protocol comprises at least one of ultrasound source frequency, peak positive pressure, pulse length, shock wave amplitude, pulse repetition frequency, and duty cycle; a monitoring system configured to distinguish boiling from cavitation in the tissue; and a controller operably coupled to the ultrasound source and the function generator, wherein the controller is configured to adjust the pulsing protocol during treatment in response to feedback from the monitoring system to induce boiling during each pulse with substantially no thermal damage to the tissue at the target site and surrounding the target site.

2. The HIFU system of claim 1 wherein the monitoring system comprises an imaging device configured to detect hyperechoic regions in the tissue.

3. The HIFU system of claim 1 wherein the monitoring system comprises a voltage probe configured to detect fluctuations in drive voltage of the ultrasound source.

4. The HIFU system of claim 1 wherein the monitoring system comprises a passive cavitation detector (PCD) having a focus aligned with a focus of the ultrasound source, the focus of the PCD being configured to detect changes in acoustic signals related to boiling.

5. The HIFU system of claim 1 wherein the monitoring system comprises a magnetic resonance imaging system configured to detect temperature and boiling activity at the target site.

6. The HIFU system of claim 1 wherein the monitoring system comprises an ultrasound imaging device configured to send and receive signals that detect the presence of bubbles in the tissue.

7. The HIFU system of claim 1 wherein the monitoring system is configured to detect the presence of boiling bubbles in the tissue.

8. The HIFU system of claim 1 wherein the pulsing protocol comprises peak positive pressure and the peak positive pressure is a result of nonlinear propagation of HIFU waves, resulting in the shock waves proximate to the target site in the tissue that at least substantially emulsify the tissue at the target site.

9. A method for treating tissue with high intensity focused ultrasound (HIFU), the method comprising: generating, from an ultrasound source, HIFU waves having a frequency range between approximately 0.5 MHz and approximately 20 MHz and a peak positive pressure between approximately 10 MPa and approximately 100 MPa; and generating a pulsing protocol used by the ultrasound source to apply the HIFU waves to a target site of tissue, wherein the pulsing protocol defines at least one of ultrasound source frequency, peak positive pressure, pulse length, shock wave amplitude, pulse repetition frequency, and duty cycle, wherein the generated HIFU waves are configured to generate shock waves in tissue at the target site distinct from shock waves resulting from cavitation; wherein the shock waves induce boiling in the tissue at the target site, and wherein the induced boiling mechanically damages the tissue at the target site with substantially no thermal damage to the tissue.

10. The method of claim 9 wherein the peak positive pressure is a result of nonlinear propagation of the HIFU waves resulting in the shock waves in the tissue at the target site that at least substantially emulsify the tissue at the target site.

11. The method of claim 9, further comprising monitoring to distinguish boiling from cavitation in the tissue at the target site.

12. The method of claim 11, wherein the monitoring comprises detecting the presence of boiling bubbles in the tissue.

13. The method of claim 11 wherein the monitoring comprises sending and receiving signals, using an ultrasound imaging device, that detect the presence of bubbles in the tissue.

14. The method of claim 11 wherein the monitoring comprises detecting hyperechoic regions in images of the tissue.

15. The method of claim 11 wherein the monitoring comprises detecting, using a voltage probe, fluctuations in drive voltage of the ultrasound source.

16. The method of claim 11 wherein the monitoring comprises aligning a focus of a passive cavitation detector with a focus of the ultrasound source to detect changes in acoustic signals related to boiling.

17. The method of claim 11 wherein the monitoring comprises detecting temperature and boiling activity at the target site using a magnetic resonance imaging system.

18. The method of claim 11, further comprising adjusting, in response to feedback from the monitoring, the pulsing protocol during treatment, wherein the ultrasound waves generated as a result of the adjusted pulsing protocol induce boiling during each pulse.

19. A high intensity focused ultrasound (HIFU) apparatus for treating tissue, the HIFU apparatus comprising: an ultrasound source configured to deliver a peak positive pressure between approximately 10 MPa and approximately 100 MPa, wherein the ultrasound source is configured to generate shock waves proximate to a target site in the tissue and distinct from shock waves resulting from cavitation; a function generator operably coupled to the ultrasound source, the function generator being configured to generate a pulsing protocol delivered by the ultrasound source to the target site of tissue, wherein the pulsing protocol comprises at least one of ultrasound source frequency, peak positive pressure, pulse length, shock wave amplitude, pulse repetition frequency, and duty cycle; a monitoring system configured to distinguish boiling from cavitation in the tissue; and a controller operably coupled to the ultrasound source and the function generator, wherein the controller is configured to adjust the pulsing protocol during treatment in response to feedback from the monitoring system to induce boiling during each pulse with substantially no thermal damage to the tissue at the target site and surrounding the target site.

* * * * *

UNITED STATES PATENT AND TRADEMARK OFFICE
CERTIFICATE OF CORRECTION

| | | |
|---|---|---|
| PATENT NO. | : 9,700,742 B2 | Page 1 of 1 |
| APPLICATION NO. | : 14/516442 | |
| DATED | : July 11, 2017 | |
| INVENTOR(S) | : Michael S. Canney et al. | |

It is certified that error appears in the above-identified patent and that said Letters Patent is hereby corrected as shown below:

In the Specification

In Column 1, Line 21, delete "This disclosure was made with government support under grant number EB007643 awarded by National Institutes of Health (NIH)–Federal Reporting and grant number SMST01601 awarded by National Space Biomedical Research Institute (NSBRI). The government has certain rights in the invention," and insert --This invention was made with government support under Grant No. EB007643 awarded by the National Institutes of Health and under Grant No. SMST01601 awarded by the National Space Biomedical Research Institute. The government has certain rights in the invention.--, therefor.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*